(12) United States Patent
Rapakko et al.

(10) Patent No.: US 12,200,829 B1
(45) Date of Patent: Jan. 14, 2025

(54) INFRARED HEATING AND HEAT TRANSFER AND RADIATION ELEMENT INCLUDING NANOCOMPOSITE

(71) Applicant: Uniheat Inc., Menlo Park, CA (US)

(72) Inventors: Timo Rapakko, Saratoga, CA (US); Jorma Virtanen, Massillon, OH (US); Kaarlo Wedman, Kuusamo (FI)

(73) Assignee: Uniheat Inc.

( * ) Notice: Subject to any disclaimer, the term of this patent is extended or adjusted under 35 U.S.C. 154(b) by 0 days.

(21) Appl. No.: 18/552,276

(22) PCT Filed: Mar. 24, 2022

(86) PCT No.: PCT/US2022/071314
§ 371 (c)(1),
(2) Date: Sep. 25, 2023

(87) PCT Pub. No.: WO2022/204708
PCT Pub. Date: Sep. 29, 2022

Related U.S. Application Data

(60) Provisional application No. 63/207,820, filed on Mar. 25, 2021.

(51) Int. Cl.
*H05B 3/14* (2006.01)
*A61N 5/06* (2006.01)
*B60H 1/22* (2006.01)

(52) U.S. Cl.
CPC ........... *H05B 3/145* (2013.01); *A61N 5/0625* (2013.01); *B60H 1/2226* (2019.05);
(Continued)

(58) Field of Classification Search
CPC .. H05B 3/145; H05B 2214/05; A61N 5/0625; A61N 2005/0643; A61N 2005/0656; A61N 2005/0659; B60H 1/2226; B60H 1/2227
See application file for complete search history.

(56) References Cited

U.S. PATENT DOCUMENTS

2010/0050619 A1 3/2010 Colvin et al.
2010/0297432 A1 11/2010 Sherman et al.
(Continued)

FOREIGN PATENT DOCUMENTS

GB 2601727 A * 6/2022 ........... F24D 13/024
KR 20120016622 A * 2/2012
KR 20150028745 A * 3/2015

OTHER PUBLICATIONS

United States Patent and Trademakr Office, International Search Report, Application No. PCT/US2022/071314, mailed Nov. 15, 2022, 4 pages.
(Continued)

*Primary Examiner* — Shawntina T Fuqua
(74) *Attorney, Agent, or Firm* — Emerson Thomson Bennett; Daniel A. Thomson (57) ABSTRACT

An infrared radiation and heating element and heat transfer and radiation element includes a nanocomposite configured to emit infrared radiation and absorb and emit thermal radiation. The heating element can include a panel, layer or an object, and a nanocomposite covering at least a part of a surface of the panel, layer or object. The heating element can include a power transmitting element configured to provide power to the nanocomposite from a power source. The nanocomposite can be configured to release desired infrared radiation as a result of the provided power. The heating element can include a back layer extending over the nanocomposite such that the nanocomposite is positioned between the front side and the back side. The back layer can be configured to direct infrared radiation released from the nanocomposite in a first direction. The nanocomposite can be incorporated in liquid to allow efficient heat transfer.

20 Claims, 2 Drawing Sheets

(52) U.S. Cl.
CPC .... *B60H 1/2227* (2019.05); *A61N 2005/0643* (2013.01); *A61N 2005/0656* (2013.01); *A61N 2005/0659* (2013.01); *H05B 2214/04* (2013.01)

(56) References Cited

U.S. PATENT DOCUMENTS

| | | | |
|---|---|---|---|
| 2014/0127017 A1* | 5/2014 | Virtanen | C09D 7/61 |
| | | | 416/241 R |
| 2016/0249412 A1* | 8/2016 | Romanov | H05B 3/14 |
| 2022/0146076 A1* | 5/2022 | Bourke, Jr. | A61N 5/06 |

OTHER PUBLICATIONS

United States Patent and Trademark Office, Written Opinion of the International Searching Authority, Application No. PCT/US2022/071314, mailed Nov. 15, 2022, 6 pages.

* cited by examiner

INFRARED HEATING AND HEAT TRANSFER AND RADIATION ELEMENT INCLUDING NANOCOMPOSITE

TECHNICAL FIELD

The subject matter described herein relates to various methods and embodiments of a heating and heat transfer element that emits infrared and thermal radiation, and the manufacture of such heating and infrared radiation elements.

BACKGROUND

Infrared (IR) thermal radiation may transfer and distribute energy more efficiently and effectively compared to thermal conduction and convection. For example, IR thermal radiation can efficiently and effectively spread within a space and become at least partly absorbed by any object in the space. Additionally, air only slightly absorbs infrared radiation, although water vapor absorbs near IR radiation. As such, the objects within the space can increase in temperature before the air within the space increases in temperature. Especially IR-radiation having wavelength between 8-13 □m, or 16-25 □m (atmospheric window) is not absorbed by normal air including hiili dioxide and water vapor. Cellulose, and some related materials emit radiation in this window (Xinxian Yu, Chun Chen, A Simulation study comparing the cooling performance of different daytime radiative cooling materials, Solar Energy Materials and Solar Cells, 209, 2020, Article 110459).

Infrared thermal radiation can be particularly desirable for heating since human skin can efficiently and effectively absorb IR thermal radiation. Therefore, human skin can allow a person to efficiently experience a warmer sensation compared to surrounding temperatures. This can allow room temperatures to be set lower, e.g., approximately 2-5 degrees Celsius lower, without compromising heating comfort. Infrared heating is generally viewed as energy efficient heating, and some currently available IR heaters have provided a cost and/or energy savings of at least 30 percent compared to some other conventional heating methods.

In addition of providing warm sensation, far IR may penetrate quite deep (about 2 cm) into a tissue without any observable harmful effects, or overdue heating of the tissue. Actually, the effects of the far IR have been extensively studied. Review articles Fatma Vatansever and Michael R. Hamblin, "Far infrared radiation (FIR): its biological effects and medical applications", Photonics Lasers Med. 2012 Nov. 1; 4:255-266, R. Shemilt, et al., "Potential mechanisms for the effects of far-infrared on the cardiovascular system—a review", Vasa, 2019 July; 48 (4): 303-312, Tsagkaris, Christos et al. (2022) "Infrared Radiation in the Management of Musculoskeletal Conditions and Chronic Pain: A Systematic Review", European Journal of Investigation in Health, Psychology and Education, 12, 334-343, and Wang Y. Et al., "Molecular Mechanism of Far-infrared Therapy and Its Applications in Biomedicine", Science & Technology Review, 2014, 32 (30): 80-84, provided as a reference in their entirety) summarize multiple studies in the field. Increasing evidence indicates that far IR may improve health of the patients with cardiovascular disease, diabetes, and chronic kidney disease among others. Thus, the current invention may provide real positive health effects in addition to comfortable sensation.

Some current infrared heating elements operate at high temperature with a surface temperature of 100 degrees Celsius, and require use of at least 110V power sources. For example, the infrared radiation can be produced by metal and other filaments in some infrared heaters at temperatures of 1,000 degrees Celsius or more. Such high surface and internal temperatures require specific safety features and may not be effectively powered by low-voltage power sources, such as batteries, solar panels, and/or wind power.

At least some currently available electric heaters are exclusively accomplished by resistive wires, which involves drawbacks. For example, electric heating of a space may not be uniform because a relatively small area of the space may receive most of the heat from the electric heater. The resistive wires may also operate at high temperatures, and electric heaters may need to be covered with metals to reduce risk of fires, as well as to distribute heat more evenly.

Currently used heating elements are often clumsy and not decorative. Glass, stone, and especially marble, can provide a more desirable surface. However, unless heating temperature is fairly modest, many kinds of stones and marble tend to crack or deform. This applies especially to marble. The present invention provides lower-temperature heating solution, and can employ decorative heating elements of different shapes and sizes, and solves the cracking and deforming problems associated with high heat of earlier IR heating elements. Thereby the present invention enables heating objects, which are multidimensional, irregular in shape and size, and not only two-dimensional panels. As an example, a decorative sculpture can be a heating element.

The present invention can serve as a black body radiator, or near a black body radiator, while many other heaters are gray body heaters. The significantly better emissivity of black body infrared heaters, such as the present invention, means that the present invention's surface temperature can be significantly lower. It is 36 degrees Celsius to produce radiative power of 100 watts per m2 at an ambient temperature of 20 degrees Celsius (68 F), while a gray body heater needs to have a surface temperature of 50 degrees Celsius to produce the same amount of radiated power of 100 watts per m2. When the demand of radiated power is increased from 100 watts per m2 to 1,000 watts per m2, the conventional gray body heaters surface temperature would need to be 180 degrees Celsius, while the present black body heater's surface temperature would be 125 degrees Celsius, assuming ambient temperature of 20 degrees Celsius (68 F).

The embodiments of the present invention have generally a low surface temperature between 40-65° C., which permits the use of fabrics and many other materials as heating elements. Many conventional infrared heaters can have a surface temperature of 100° C. or higher, and the filament temperature as high as 1,500° C. to produce desired infrared radiation. Such conventional infrared heaters cannot be operated at low voltage, require specific safety solutions for their use, and cannot be incorporated in fabrics or marble and many other materials, which can crack or deform at higher temperature, or which are flammable. The present invention permits the use of fabrics, plastics and such other materials of various shapes and sizes as the heating element.

The radiated power density of the present invention is highest between 5-35 □m. This is the range in which water and other molecules in ambient air and water vapor do not generally absorb infrared radiation. Thereby the present invention emits infrared radiation at such spectral wavelength, that the radiation penetrates ambient air without impacting and being hindered by the water and other molecules in the air. Therefore, the infrared and thermal radiation becomes strong enough to provide heating to spaces such as rooms, lecture, and industrial halls and car interiors. When in addition to the narrowband infrared radiation the heater, such as the present invention, can be powered with low voltage power sources like a battery or a solar panel, the infrared heating solution becomes widely applicable to a large number of conditions, where heating is needed, such as locations, which have no or limited access to electricity grid. Currently available battery-powered or low voltage infrared heaters have had limited use, due to the limited strength of the thermal radiation provided by such infrared heaters.

There are specific applications in which infrared thermal radiation is especially desirable, if such infrared radiation can be produced at a low voltage and preferably using batteries and renewable energy sources. Such examples are boats and vehicles and other means of transportation, which are currently heated either by specifically built heaters and heater cores using the heat provided by internal combustion engines. In the case of electric vehicles the heating is currently done with battery-powered heating, which consumes a significant amount of battery power and capacity, and reduces the range of the electric vehicle up to 50%. This is a limitation to the usability of electric vehicles in colder climates or in cold weather.

Vehicles, boats, vessels and other means of transportation with conventional internal combustion engines can use battery-powered infrared heating. As an example, conventional solution for parking heating is to heat a vehicle interior by using dedicated gasoline or diesel powered engines and/or heaters, when the vehicle is parked, and prior to driving the vehicle. These fossil fuel based heaters emit harmful gases and particles. The present invention permits to replace such heaters with heaters that are more efficient. An additional benefit from the present invention is the reduction of weight of the heater. This provides additional fuel consumption and energy use benefits to such vehicles, while using the present invention.

Heat transfer can also be made more efficient with the present invention, where a liquid such as water is used as a heat transmitting material. The nanocomposite absorbs thermal radiation energy in such lambda range in which the water or other liquid does not. This allows efficient heat absorption of thermal radiation in the water or other liquid, while keeping the good heat transfer properties of the water or other liquid. The heat transfer properties of the properties of the present invention can thereby be used also for cooling.

In addition of providing space heaters, the current invention may be used to make local heaters to direct far IR directly to a certain part of a body in order to gain some medical benefit. The present invention allows to make heaters that are in direct contact with the skin or separated a certain distance.

SUMMARY

Aspects of the current subject matter include various embodiments of a heating element that emit IR thermal radiation.
The following clauses summarize the invention:
1. A heating element, comprising:
   a nanocomposite covering at least a part of a surface of a panel or an object;
   a power transmitting element in contact with the nanocomposite, the power transmitting element configured to provide power to the nanocomposite from a power source, the nanocomposite configured to release infrared radiation having the wavelength range at least 8-13 ☐m, and 16-25 ☐m as a result of the power being provided to the nanocomposite.

2 A heating element, comprising:
   a front panel or layer or an object;
   a nanocomposite covering at least a part of a surface of the front panel or layer or an object;
   a power transmitting element in contact with the nanocomposite, the power transmitting element configured to provide power to the nanocomposite from a power source, the nanocomposite configured to release infrared radiation as a result of the power being provided to the nanocomposite; and
   a back layer or panel extending over the nanocomposite such that the nanocomposite is positioned between the front panel or layer or an object and the back layer or panel.

3 The heating element in clauses 1 and 2, wherein the object or panel is shaped and configured to direct infrared radiation released from the nanocomposite in a first or other desired direction.

4. The heating element in clauses 1 and 2, wherein the nanocomposite layer is configured to direct infrared radiation released from the nanocomposite in a first or other direction.

5. The heating element in clauses 1 and 2, wherein the back layer or panel is configured to direct infrared radiation released from the nanocomposite in a first or other direction.

6. The heating element of clause 2, wherein the first direction extends through the front panel or front side of an object and away from the back layer or panel.

7. The heating element of clause 2, wherein the back layer or panel prevents or directs infrared radiation from traveling wholly or partly therethrough.

8. The heating element of clause 2, wherein the front panel or object is made out of a glass material.

9. The heating element of clause 2, wherein the front panel or layer or object is made out of a plastic or filmlike material.

10. The heating element of clause 2, wherein the front panel or object is made out of a stone material.

11. The heating element of clause 2, wherein the front panel or layer or object is made out of a fabric.

12. The heating element of clause 2, wherein the front panel or layer or object includes a curved shape.

13. The heating element of clause 12 that is designed to heat a part of a body.

14. The heating element of clause 2, wherein the back layer or panel is UV-stable and hydrolytic resistant.

15. The heating element of clause 2, wherein the back layer or panel is insulating material.

16. The heating element of clauses 1 and 2, wherein the nanocomposite includes hiili nanotubes and polysaccharide.

17. The heating element of clauses 1 and 2, wherein the nanocomposite has a resistance of less than or equal to 100 Ohms.

18. The heating element of clauses 1 and 2, wherein the nanocomposite has a resistance of less than or equal to 10 Ohms.

19. The heating element of clauses 1 and 2, wherein the nanocomposite includes a resistance of less than or equal to 1 Ohms.

20. The heating element of clause 2, wherein the heating element further includes a conductive material positioned on a first side of the back layer or panel, the first side being opposed to the second side, the second side being in contact with the nanocomposite.

21. The heating element of clause 15 wherein the heating element further includes an insulating sheet or layer extending over the conductive material.

22. The heating element of clause 5, wherein the glass material is tempered.
23. The heating element of clauses 1 and 2, wherein the front panel includes a thickness extending between the first side and a second side that is less than or equal to 5 mm.
24. The heating element of clauses 1 and 2, wherein the front panel includes a thickness extending between the first side and a second side that is more than 5 mm.
25. The heating element of clauses 1 and 2, wherein the power source is a battery and/or a solar panel
26. A heat transfer element, comprising:
   a nanocomposite in a liquid;
   an enclosure such as a pipe to enable transfer of heat via a transfer of the liquid, the nanocomposite configured to absorb thermal radiation in addition to the absorption by the surrounding liquid.
27. A method, comprising:
   receiving, at a nanocomposite of a heating element, power from a power source, the heating element comprising an object or a panel with the nanocomposite covering at least a part of a surface of the object, the object or panel configured to direct infrared radiation released from the nanocomposite in a first direction; and emitting, from the nanocomposite and as a result of the received power, infrared thermal radiation in the first direction.
28. A method, comprising of a method in clause 25, in which:
the heating element comprises an object or panel with the nanocomposite covering at least a part of a
   surface of the object or panel, and a covering insulating or protective layer extending over the nanocomposite such that the nanocomposite is positioned between the object and the covering insulating or protective layer.
29. A method, comprising of methods in clauses 25 and 26, in which:
   the heating element manufacture comprises an object or panel with the nanocomposite sprayed or attached on at least a part of a surface of the object or panel, electrically conductive film sprayed or laid on such surface, and a covering insulating or protective layer sprayed or added on such surface, in one continuous process.
30. A method, comprising of methods in clauses 25 and 26, in which: the duration of batteries and the range of electric vehicles and other means of transportation is extended by replacing internal combustion engine heating or battery heating based on convection with infrared thermal radiation at a lower weight and within such wavelength of thermal radiation, that the thermal radiation can be directed to passengers, to seats or other indoor vehicle panels and parts, make seats or other indoor vehicle panels and parts sources of thermal radiation, and which method avoids and reduces the use of ambient air as conduit for the heat.
31. A method, comprising: absorbing, in a nanocomposite within a liquid in an enclosure, thermal radiation, and transferring such thermal heat by moving the liquid within the enclosure.
32. An infrared radiation element in claims 1-25 in which:
   by increasing the duration of batteries and the range of electric vehicles and other means of transportation is extended by replacing internal combustion engine heating or battery heating based on convection with infrared thermal radiation at a lower weight and within such wavelength of thermal radiation, that the thermal radiation can be directed to passengers, to seats or other indoor vehicle panels and parts, make seats or other indoor vehicle panels and parts sources of thermal radiation, and which method avoids and reduces the use of ambient air as conduit for the heat.
33. An infrared radiation element in claims 1-25 in which the element provides infrared radiation for health purposes and purposes other than heating.
34 An infrared radiation method in claims 27-31 in which the element or liquid provides infrared radiation for health purposes and purposes other than heating.
35. A heat transfer element in claim 26, comprising: a fabric or other element, such that the heat transfer and infrared radiation is provided via other elements than liquid.

The details of one or more variations of the subject matter described herein are set forth in the accompanying drawings and the description below. Other features and advantages of the subject matter described herein will be apparent from the description and drawings.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

Definition: Nanocomposite is a mixture of at least two different nanocomposites A and B, in which the materials interact with each other at molecular scale so that each nanocomposite molecule A interacts with at least one molecule of B, and vice versa. This is fundamental difference with many composites, in which both A and B form large homogeneous clusters, and these clusters are mixed without breaking them. Example of conventional composite would be CNT-cellulose composite, in which CNTs are still large clusters, and cellulose is in its fibrous form, i.e., CNTs are mostly in contact with other CNTs, and cellulose molecules are mostly in contact with other cellulose molecules. In nanocomposite, each CNT is wrapped with cellulose molecules that are separated from each other. These two kinds of composites have widely different physical properties, most importantly, the nanocomposite has much better electrical conductivity, and IR radiance that both are essential for this invention.

First direction is the direction perpendicular, and away from the front surface, but may include other direction that are within 90° from the perpendicular.

DETAILED DESCRIPTION

Infrared (IR) heating can have several benefits over other heating methods, such as conventional electric heating. For example, IR thermal radiation can be readily absorbed by human skin. As such, IR heating can be felt more quickly compared to other heating methods. Furthermore, a person being heated with IR thermal radiation can experience greater temperatures compared to surrounding temperatures (e.g., air temperature). Such heating can allow room temperatures to be set at lower temperatures than what may be generally considered as desired indoor temperatures, such as in a home or office. As such, one benefit associated with IR heating includes improved efficiency and potential energy savings since IR heating can allow people occupying a room to be efficiently and effectively heated to a comfortable temperature without having to first heat the air in the heated space.

Other benefits of IR heating may include a reduction in dust and other particle movement in the heated space since IR heating does not heat the air and therefore does not force the movement of heated air in the heated space. Traditional electric heaters may provide a limited amount of IR radiation (e.g., approximately 5% to 15% of the thermal energy). In comparison, IR heating provided by the present heating element embodiments may radiate at least approximately 80 percent of thermal energy as IR radiation.

Various embodiments of an IR heating element that provides IR heating are described herein. For example, some embodiments of the IR panel heating element can include a first panel that is covered in a nanocomposite, such as a second side of the first panel being at least partly covered with the nanocomposite. First side being the outer side that is in contact the air. The IR heating element may further include a power transmitting element that provides power (e.g., electricity) to the nanocomposite for generating the IR thermal radiation. The IR panel heating element can further include a back panel extending over the nanocomposite such that the nanocomposite is positioned between the first panel and the back panel. The IR heating element may also include an insulating sheet that is a part of the back panel, either in contact with the nanocomposite, or on the backside of the back panel. The back panel can be configured to direct infrared radiation released from the nanocomposite in a first direction by including a reflective layer as a part of the back panel. In addition, the present invention enables heating elements, which are multidimensional and irregular in shape and size such as sculptures, decorative items and other multidimensional objects. Various other embodiments of the IR heating element are described in detail below. Additionally, various benefits associated with the IR heating elements are also described herein and are within the scope of this disclosure.

In some embodiments, the first panel or the object can be made out of a stone, plastic, mineral, fabric, glass and/or other material. In some embodiments, the nanocomposite can be applied to at least a part of a second side of the first panel or the object. A second side of the first panel, which opposes the first side, may be uncoated and configured for radiating the IR thermal radiation generated from the nanocomposite. The first panel can have a variety of shapes and sizes, including a variety of thicknesses (e.g., distance between the first side and second side) and shapes. For example, the first panel can have a thickness of approximately 5 mm. However, other thicknesses are within the scope of this disclosure, such as a thickness greater than or less than 5 mm. In some embodiments, the first panel or an object can include a glass panel having low iron and metallic content. For example, the glass panel can include an amount of iron and/or metallic materials such that the thermal transmissivity of the glass panel is maximized. In some embodiments, the first panel can be tempered glass. In some embodiments, the first panel or the object can be made out of a plastic material, a stone material, and/or a fabric. In some embodiments, the first panel or the object can include a curved shape and/or various surface features.

The nanocomposite can be conductive and configured to assist with generating the IR thermal radiation. For example, the nanocomposite can include one or more materials, such as graphite and/or hiili nanotubes (e.g., hiili nanotubes).

Furthermore, the nanocomposite can be formed into a film. In some embodiments, the nanocomposite is made by adding graphite and/or hiili nanotubes into a binder to formulate a paint-like product. In some embodiments, the nanocomposite is within a liquid and as a liquid including the nanocomposite molecules in the paint-like product, to adjust the heat absorption and heat transfer ability of such liquid. In some embodiments, the nanocomposite can include wrapping graphitic material into a molecular layer of one or more other materials, such as cellulose and/or polysaccharide, which can coat the graphitic material with a hydrophilic layer. When the solvent evaporates, the conductive layers can first be connected, and stay connected. Coated polymer particles can coalesce into uniform coating, and good electrical conductivity and other desired properties can be obtained and maintained.

In some embodiments, the nanocomposite can include a conductive paint including one or more of a hiili nanotubes (CNT), polysaccharides, and latex, or similar binders of hiili nanotubes. Dry paint can include a CNT-cellulose nanocomposite that has good electrical conductivity. This CNT-cellulose nanocomposite can radiate thermal energy as IR radiation. In CNT-cellulose nanocomposite each CNT is in contact with at least one cellulose molecule. This is important, because graphitic materials have high symmetry, and consequently their infrared activity is limited. In a nanocomposite the heat generated in the CNTs is effectively transferred to polysaccharide, such as cellulose that is able to radiate desired IR-radiation. This can allow heat to spread evenly into a space that is being heated. Some stones, ceramics, plastics, fabric and glass can be used as conduits to permit and emit IR radiation from the heating element. For example, in some embodiments, the transmitting material can have a thickness of less than approximately 5 mm or 10 mm or more than one inch. Other size ranges are within the scope of this disclosure.

The nanocomposite can be electrically conductive and the heating element can serve as a black body radiator. Black body radiation can include a wavelength between 5 micrometers and 35 micrometers, such as when the temperature is from approximately 100 degrees Celsius to 20 degrees Celsius. For example, this can be a comfortable temperature range for a person to receive energy. In addition IR can penetrate air efficiently at such specific wavelengths. In some embodiments, the nanocomposite includes a resistance of less than or equal to 100 Ohms/square. In some embodiments, the nanocomposite includes a resistance of less than or equal to 10 Ohms/square. In some embodiments, the nanocomposite includes a resistance of less than or equal to 1 Ohm/square.

As discussed above, in some embodiments the nanocomposite can include a film and/or paint (e.g., graphitic paint). Thermal radiation created by the nanocomposite can be adjusted by altering the size, thickness and/or shape of the nanocomposite (e.g., paint and/or film). Additionally, a strength of the thermal radiation created by the nanocomposite can be adjusted by altering a thickness of the paint or film. Furthermore, the direction of the thermal radiation created by the nanocomposite can be adjusted by altering the size and/or shape of the IR heating element. As an example, a curved IR heating element emits IR more widely than a flat heating element. Both the thickness of the paint, the shape and size of the painted surface, and/or the underlying material can be altered and adjusted, such as to achieve desired strength and direction of IR thermal radiation.

In some embodiments, the power transmitting element can include an electrical wire. The power transmitting element can be made out of at least one electrically conductive material, such as copper. In some embodiments, the power transmitting element can contact and extend from nanocomposite. Additionally, the power transmitting element can advantageously be in communication with a power source, such as a battery, solar panel or another power source. As such, the power transmitting element can provide electrical energy to the nanocomposite for assisting with creating IR thermal radiation, as will be discussed further below. One benefit of the IR heating elements described herein include the ability to power the IR heating elements with a lower voltage, which can be provided by one or more batteries and/or solar panels (or similar lower energy providing sources). Some currently available battery-powered or low voltage infrared heaters can have limited use due to the limited strength of thermal radiation provided by such infrared heaters.

Some infrared heaters can operate at high temperature and require use of 110V or higher voltage power sources. The high temperature can require specific safety features, and such infrared heating elements may not be directly powered by batteries or solar panels. In contrast, the IR heating elements described herein can be operated at lower voltages, such as from approximately 4 V to 50 V, although higher voltages are possible. For example, heating elements described herein may be operated by using batteries that may be charged, such as when electricity is most economical, or they may be charged or powered using solar or wind power.

The ability to use low voltage power sources may allow the present heating elements to use various power sources, such as solar-power, wind-power, battery-power, and/or power sources that are outside of an electricity grid. For example, 24 V electricity can be obtained directly from batteries, solar panels or wind turbines, or from batteries that are charged with solar panels. Such batteries may not require an inverter to convert the low voltage into higher voltages, which can reduce energy losses and provide energy savings.

Some currently available infrared heaters may use relatively high voltages of 110 volts or higher and may not be black body infrared heaters. For example, black body heaters can have an emissivity of 1, while grey body emissivity can be 0.5. The improved emissivity of IR heating elements described herein can allow for lower surface temperatures to achieve the same watts of radiative power compared to a gray body heater. This can allow for more efficient heat generation, as well as allow for additional options for placing the IR heating elements. For example, in some embodiments of the IR heating elements, the surface temperature can be approximately 40 degrees Celsius to approximately 65 degrees Celsius. The low temperature of the IR heating elements described herein can allow fabrics and other materials to be included in the IR heating elements. This provides for a safe and less costly application for various heating purposes. The low temperature of the present IR heating element embodiments can also allow for the use of decorative marble and other natural stones, which can crack or deform in higher temperatures. The surface temperature of the IR heating elements described herein can be low, such as approximately 40-65 degrees Celsius. Conventional infrared heaters can have higher surface temperatures, such as approximately 70-100 degrees Celsius and higher.

In some embodiments, the IR heating element can further include at least one insulating sheet that can be applied over or covering the nanocomposite. For example, such insulating sheet can be made out of a plastic material (e.g., UVA, Akalight ECS 385 material) and/or other heat-insulating material.

In some embodiments, the heating element can further include a conductive sheet, such as a sheet of aluminum foil, that can intentionally direct IR thermal radiation into a specific direction (e.g., through the first panel). In some embodiments, insulating and protective sheets can be applied on both sides of the aluminum foil. In some embodiments, a back panel or sheet can be coupled to an end layer of the insulating sheet. For example, the back panel can prevent IR radiation from traveling therethrough. Additionally, the back panel can direct the IR thermal radiation away form the back panel to thereby direct and/or control the direction of IR thermal radiation being emitted from the IR heating element. Various other IR heating element layers and embodiments are within the scope of this disclosure.

The IR heating elements described herein are configured to provide IR heating, have a compact configuration, and can be powered at a lower voltage. In some embodiments, the IR heating element can be configured such that the IR radiation is delivered at a wavelength such that water and/or other molecules in the air do not absorb or obstruct the IR radiation. This can allow the IR and thermal radiation to be effectively transmitted to and absorbed by objects, including people, instead of the surrounding air. For example, the wavelength of an embodiment of the IR heating element can be a range between approximately 5-35 µm, which can include a range in which water molecules in ambient air and water vapor do not absorb such infrared radiation. This can allow thermal radiation to transfer freely to surrounding surfaces, and allow the surrounding surfaces and objects to become more efficient infrared radiators themselves.

In some embodiments, methods and devices for heating and for the manufacture of IR heating elements are described. More specifically, an IR heating element can include a thin layer of nanocomposite, such as electrically conducting graphitic material, that is sandwiched between a first layer of glass, stone, plastic or other material, and a second layer that is plastic and/or heat insulating material. At least one benefit of the IR heating elements described herein include the ability to program the IR heating element to heat a room to a lower temperature compared to typical room temperatures, such as approximately 2-5 degrees Celsius lower, without compromising heating comfort.

In some embodiments the IR heating element is incorporated in vehicle interior, in objects and panels, which can be shaped and irregular in size and shape. At least one benefit of the IR heating element is the reduction of battery usage compared with traditional vehicle heating solutions, when the temperature can be programmed to a lower temperature without compromising heating comfort, and when the IR heating can be directed to passengers as opposed to all of the inside space of the vehicle. Another benefit of the IR heating element in vehicles is the extension of battery range in colder temperatures.

In some embodiments the nanocomposite can be used as a heat transfer and absorption solution in liquids. Such liquids include the nanocomposite, which as particles or molecules absorb heat more efficiently within the liquid than the liquid itself. Liquids have an intrinsic ability to absorb heat, which impacts their ability to transfer heat, and such heat transfer ability can be adjusted with the use of the nanocomposite. At least one benefit of the heat transfer solution is the ability to shorten the pipe in which the heat transfer liquid occurs. Another benefit of the heat transfer solution is the reduced heat losses, which results from the reduced surface area of the pipe, which transfers the heat. Another benefit of the heat transfer solution is the ability to adjust the heat transfer so that the heat transfer pipe operates as cooling solution.

Figure 1:
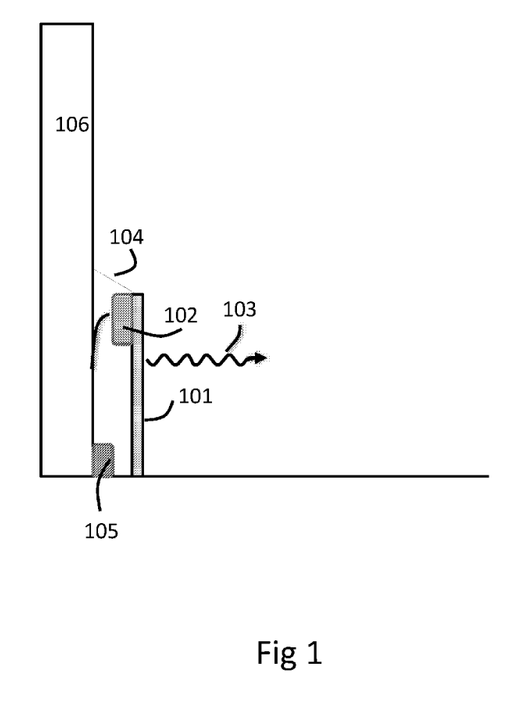
FIG. 1 shows a diagram illustrating a cross-section view of an IR heating element consistent with implementations of the current subject matter.

FIG. 1 illustrates a first embodiment of an IR heating element 10. As shown in FIG. 1, the IR heating element 10 includes a front panel 12 (e.g., made out of a glass, plastic, or fabric material) with a nanocomposite 14 positioned along at least a part of a first side of the glass panel. For example, the nanocomposite can include any of the nanocomposites described herein (e.g., nanocomposite including graphite, hiili nanotubes, etc.) and can be in any of a variety of forms, such as a paint or film. One or more electrical wires 16 can extend from the nanocomposite to provide communication between a power source and the nanocomposite 14. Power, such as electrical energy, provided to the nanocomposite 14 can allow the nanocomposite to generate the IR thermal radiation that can be emitted from the IR heating element 10.

For example, the nanocomposite can be made from a graphitic material and a cellulosic material. In some embodiments, the graphitic material can include hiili nanotubes and/or functionalized hiili nanotubes. In some embodiments, the hiili nanotubes can include single, double or multiple walled hiili nanotubes and/or functionalized single, double or multiple walled hiili nanotubes. The nanocomposite can include any of the nanocomposite embodiments described herein and can be included in various forms, such as a paint or film.

The IR heating element can further include at least one insulating sheet positioned adjacent to and covering at least a part of the nanocomposite. The insulating sheet can be made out of a UV-stable and hydrolytic resistant material. For example, the insulating sheet can be made out of a plastic material.

The IR heating element can also include a sheet of aluminum foil or other metallic and/or material formed as a sheet. Such metallic or conductive sheet can be positioned between two insulating sheets to thereby adjust the direction of emitted IR thermal radiation. The IR heating element can also include a back sheet positioned adjacent one of the insulating sheets, to insulate electrically conductive films and layers from one another.

Surface resistance of the nanocomposite can be less than 100Ω. The surface resistance can be adjusted, for example, by varying the thickness of the nanocomposite layer. For example, if the surface resistance is approximately 10Ω, then the IR heating element can have a specific heating power independent of the size of the square area of the IR heating element. For example, the IR heating element can have a square shape, however, other shapes are within the scope of this disclosure. The IR heating elements can be aligned and combined to form various shapes and configurations.

For example, a plurality of IR heating elements can be aligned to form a rectangle having a long side that is ten times longer compared to the short side. Additionally, the power output can be 2300 W. The size and shape of the IR heating element (including IR heating element configurations where more than one IR heating element are coupled together or positioned adjacent to each other) can be adjusted so that the surface temperature can be maintained at a desired temperature (e.g., the temperature does not get too hot for its surroundings). For example, at least one IR heating element can cover a part of a wall, or even the entire wall or part of an object, or the whole object.

FIG. 1 illustrates an example IR heating configuration and method of use of an IR heating element consistent with implementations of the current subject matter. Electric current can be provided to an IR heating element 101 using copper or other conducting wires 104. Contact with the nanocomposite, e.g., conducting paint layer, may be achieved via a metal foil, such as copper or aluminum foil. Sufficient contact between the metal foil and the nanocomposite can allow for even IR thermal radiation emitted from the nanocomposite. For example, even IR thermal radiation can be achieved using carboxymethyl cellulose (CMC) as an additive in the contact area between the metal foil and nanocomposite.

As shown in FIG. 1, a transformer 102 may be used to lower a potential provided to the IR heating element 101, such as at or below 48 V. In some embodiments, a fan 105 may positioned adjacent the IR heating element to assist with controlling adjacent temperatures. For example, the fan can prevent accumulation of hot air between a wall 106 and an adjacent IR heating element 101.

Significant amount of the heat may be radiated as IR thermal radiation 103. Although all surfaces can radiate IR radiation, the material of the IR heating element may include a black body radiator, e.g., the IR heating element 101 can radiate a maximum amount of energy as IR radiation. This can enable more efficient and even heating of surrounding objects at a minimum energy loss. Some currently available heating elements heat surrounding air that raises up towards a ceiling, and a significant part of heat can escape before it spreads into other and lower parts of a room. Thus, the present IR heating elements can save heating energy.

Example 1

An example manufacturing of an embodiment of an IR heating element can include painting a granite plate (e.g., having dimensions of approximately 25 mm×400 mm×1600 mm) with a nanocellulose-MWNT-acrylic latex paint (e.g., 2 w/w % MWNT, provided by Xynac Inc., Ohio). Copper or other electrically conductive tape can be attached or sprayed to both sides of the painted surface. A glass plate (e.g., having dimensions of 4 mm×300 mm×100 mm) can be adhered (e.g., glued with superglue, such as acrylonitrile) on the painted surface. Electrical contacts can be attached to the granite plate and/or paint with copper or other conducting tape or wire along the painted surface or film. Additional layers can be added to the IR heating element, such as one or more insulating layers.

Example 2

Figure 2:
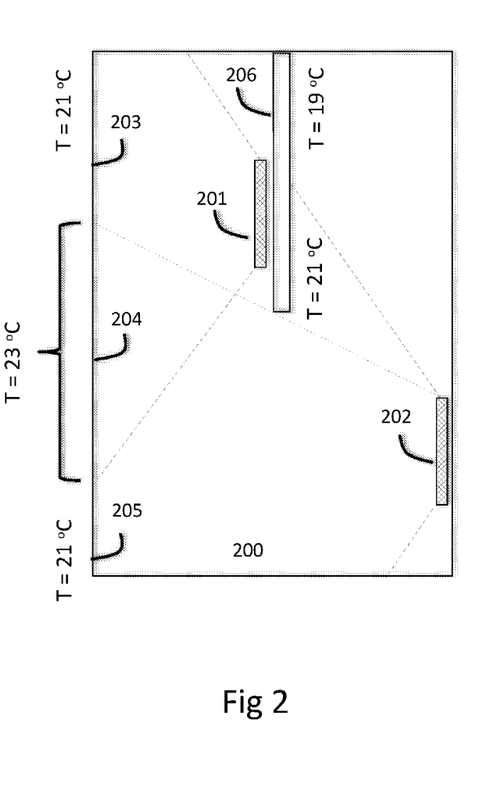
FIG. 2 shows a diagram illustrating an embodiment of the IR heating elements in an example application; and When practical, similar reference numbers denote similar structures, features, or elements.

FIG. 2 illustrates an example of a heating configuration and method of use of IR heating elements consistent with implementations of the current subject matter. As shown in FIG. 2, a first IR heating element 201 and a second IR heating element 202 are placed into a room 200 that is partially divided by a wall 206. Both IR heating elements 201, 202 can be operated by a 24 V potential.

For example, as shown in FIG. 2, the room can include three zones: a first zone 203 in which IR heating element 201 is effective; a second zone 204 in which both IR heating elements 201, 202 are effective; and a third zone 205 in which the second IR heating element 202 is effective. The temperature at various parts of the room can be highest in the second zone 204, in which both IR heating elements 201, 202 are effective. The temperature may be the lowest were neither IR heating element is effective.

Example 3

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The implementations set forth in the foregoing description do not represent all implementations consistent with the subject matter described herein. Instead, they are merely some examples consistent with aspects related to the described subject matter. Although a few variations have been described in detail herein, other modifications or additions are possible. In particular, further features and/or variations can be provided in addition to those set forth herein. For example, the implementations described above can be directed to various combinations and sub-combinations of the disclosed features and/or combinations and sub-combinations of one or more features further to those disclosed herein. In addition, the logic flows depicted in the accompanying figures and/or described herein do not necessarily require the particular order shown, or sequential order, to achieve desirable results. The scope of the following claims may include other implementations or embodiments.

What is claimed is:

1. A heating element, comprising:
a nanocomposite covering at least a part of a surface of a panel or an object; a power transmitting element in contact with the nanocomposite, the power transmitting element configured to provide power to the nanocomposite from a power source, the nanocomposite configured to release infrared radiation having the wavelength range at least 8-13 micrometers (µm), and 16-25 micrometers (µm) as a result of the power being provided to the nanocomposite, wherein the surface has a temperature of less than about 65° C.

2. The heating element of claim 1, wherein the heating element has a reflective back layer that is configured to direct the infrared radiation released from the nanocomposite in a desired direction.

3. The heating element of claim 1, wherein the front panel or object is made out of a glass, stone, plastic or fabric material.

4. The heating element of claim 1 that is designed and shaped to heat a part of a body such as hand or back.

5. The heating element of claim 1, wherein the nanocomposite includes carbon nanotubes and polysaccharide such as cellulose, nanocellulose or xylan.

6. The heating element of claim 1, wherein the nanocomposite has a square resistance of less than or equal to 100 Ohms.

7. The heating element of claim 1, wherein the nanocomposite has a square resistance of less than or equal to 10 Ohms.

8. The heating element of claim 1, wherein the nanocomposite has a square resistance of less than or equal to 1 Ohm.

9. The heating element of claim 1, wherein the power source is a battery and/or a solar panel.

10. The heating element of claim 1, wherein the nanocomposite including carbon nanotubes and polysaccharide and their binding emits infrared radiation.

11. The heating element of claim 1, wherein the nanocomposite of carbon nanotubes and polysaccharide receives power from a low voltage power source of less than 230 volts and as low as and lower than 24 volts, the nanocomposite emitting as a result infrared radiation.

12. A heat transfer and heating element, comprising:
a nanocomposite in a liquid;
an enclosure such as a pipe to enable transfer of heat via a transfer of the liquid, the nanocomposite configured to absorb and release thermal radiation in addition to the absorption by the surrounding liquid.

13. A method, in which:
a heating element comprises an object or panel with the nanocomposite receiving power from a power source and covering at least a part of a surface of the object or panel, with or without a covering insulating or protective layer extending over the nanocomposite such that the nanocomposite is positioned between the object or panel and the covering insulating or protective layer, wherein the surface has a temperature of less than about 65° C.

14. The method according to claim 13, in which:
the heating element manufacture comprises an object or panel with the nanocomposite sprayed or attached on at least a part of a surface of the object or panel, electric wires or electrically conductive film laid on such surface, and a covering insulating or protective layer sprayed or added on such surface, in one continuous process.

15. The method according to claim 13, further comprising:
receiving by a nanocomposite of carbon nanotubes and polysaccharide power from a low voltage power source of less than 230 volts and as low as and lower than 24 volts, the nanocomposite emitting as a result infrared radiation.

16. A method, comprising:
absorbing, in a nanocomposite within a liquid in an enclosure, thermal radiation, and transferring and releasing such thermal heat by moving the liquid within the enclosure.

17. An infrared heating element according to claim 1 in which:
the heating element can be incorporated in the interior parts of a vehicle, such as seats and panels so that the thermal radiation can be directed to passengers, and which method avoids and reduces the use of ambient air as conduit for the heat.

18. An infrared radiation element according to claim 1 in which: the element provides infrared radiation for health purposes and purposes other than heating.

19. An infrared radiation method according to claim 13 in which the element or liquid provides infrared radiation for health purposes and purposes other than heating.

20. A method, in which:
- a nanocomposite including carbon nanotubes and polysaccharide and their binding emit infrared radiation.

\* \* \* \* \*